United States Patent
Brown

Patent Number: 6,026,518
Date of Patent: Feb. 22, 2000

[54] FOREHEAD PERSPIRATION COLLECTION AND TRANSFER DEVICE IN AN EYEGLASS FRAME

[76] Inventor: Robert L. Brown, 4800 W. Anton Rd., Tucson, Ariz. 85746

[21] Appl. No.: 09/058,379

[22] Filed: Apr. 9, 1998

Related U.S. Application Data

[63] Continuation-in-part of application No. 08/565,831, Dec. 1, 1995, abandoned, which is a continuation-in-part of application No. 08/697,479, Aug. 26, 1996, Pat. No. 5,740,556, which is a continuation-in-part of application No. 08/862,604, May 23, 1997, Pat. No. 5,781,932.

[51] Int. Cl.[7] ............................................. A61F 9/02
[52] U.S. Cl. ............................... 2/439; 2/181.6; 2/181.8; 351/62
[58] Field of Search ........................ 2/181, 181.6, 181.8, 2/181.2, 182.8, 171.2, 174, 209.13, 452, 439, 426, 435, 436, 437, 448, 425, 11, 12, 15, DIG. 11; 351/41, 44, 62, 123, 158

[56] References Cited

U.S. PATENT DOCUMENTS

| | | | |
|---|---|---|---|
| 540,746 | 6/1895 | Lamb | 2/439 |
| 1,750,937 | 3/1930 | Morgan | 2/174 |
| 2,320,782 | 6/1943 | Larsen | 2/171 |
| 4,130,902 | 12/1978 | Mackenroth, III et al. | 2/171.2 |
| 4,393,519 | 7/1983 | Nicastro . | |
| 4,616,367 | 10/1986 | Jean et al. . | |
| 4,626,247 | 12/1986 | Frankel | 2/DIG. 11 |
| 4,638,512 | 1/1987 | Frankel | 2/174 |
| 4,885,808 | 12/1989 | Carpenter . | |
| 4,951,316 | 8/1990 | Moody | 2/10 |
| 4,955,087 | 9/1990 | Perez . | |
| 5,056,163 | 10/1991 | Chou | 2/181 |
| 5,309,577 | 5/1994 | Buononato | 2/452 |
| 5,319,396 | 6/1994 | Cesarczyk | 351/62 |
| 5,428,411 | 6/1995 | Kopfer | 351/62 |

*Primary Examiner*—Amy B. Vanatta

[57] ABSTRACT

An eyewear lens frame constructed of plastic and rubber like materials that has the added advantage of collecting, transferring and disposing of forehead perspiration through its member parts. Perspiration runoff is captured via a lip seal where it becomes congregated in a collection trough. Excess run off flows through the absorption cutouts where they amass in the frame canal. These fluids become gravitationally expelled out the ends of the frame arms via an inter connecting network of canals.

1 Claim, 3 Drawing Sheets

FOREHEAD PERSPIRATION COLLECTION AND TRANSFER DEVICE IN AN EYEGLASS FRAME

This is a continuation-in-part of Ser. No.08/862,604, filed May 23, 1997, now U.S. Pat. No. 5,781,932, which is a continuation-in-part of Ser. No. 08/697,479, filed Aug. 26, 1996, now U.S. Pat. No. 5,740,556, which is a continuation-in-part of Ser. No. 08/565,831, filed Dec. 1, 1995, now abandoned.

BACKGROUND OF THE PRESENT INVENTION

This invention relates to articles that absorb sweat from the forehead. Such devices are usually constructed of spongy or cloth materials that tend to capture perspiration runoff until its absorbing mass becomes saturated. These products are usually referred to as sweat bands. In recent years a number of different strategies have been applied toward sweat bands. Consequently a number of devices have been created to confront the annoying problem of forehead perspiration runoff.

BACKGROUND-DESCRIPTION OF PRIOR ART

While most of us work and live through the usual seasonal climatic changes it is normal for people to become exposed to the hot days of summer. The temperature and humidity extremes will vary according to geographic and atmospheric conditions. These are the times and circumstances that cause profuse forehead perspiration. It happens quite often that sweat from the forehead drips down upon the lenses of eyeglass wearers or even into peoples eyes causing a degree of annoying aggravation. Many individuals would welcome a device that would deal with this problem effectively if it could be incorporated as an added feature into an article that is already commonly worn such as eyeglasses.

What is presently available are articles that are all similar in that they are composed of the familiar fluid absorbing materials such as cloth fibers and sponge. They are generally adaptive to the head as a head band which is either wide and thick all the way around the head or primarily just in front. Some of them use straps or more rigid bulky structures that contain lenses and or sweat absorbing fabrics.

One such article illustrates a combination visor with sweatband and eye shield. The device appears common because essentially it is just a common sweat band with the addition of a visor and lens member.

Another device is a common sweatband with the addition of flip up lenses using a spring member and is similar to the above described article.

Another similar device is a common strap sweat band utilizing flip up lenses which can be accomplished independently for each eye so a positional lens adjustment relative to the eye can be achieved. Like most sweat bands they are only some what effective at stopping forehead perspiration runoff until saturation of their absorbing element occurs.

Yet another apparatus is similar to those described above being essentially a sweat band with a dark lens that Functions as a visor in the up position and as a lens in the down position.

Another article features a buoyant thin strap with attached sun protective lenses designed to float so they can be retrieved more easily when lost while engaged in water borne activities. This device does not appear to confront forehead perspiration problems.

There are other examples of like articles as described above but none consider any unique alternatives to the capture and disposal of fore head perspiration that could be inherent in either a sweat band or eyeglasses.

SUMMARY OF THE INVENTION

This invention is comprised primarily of molded and or injected elements whose components are inter connective to one another. The completed device will submit an eye wear lens frame capable of satisfying the traditional requirements of eye glass frames with the added capability of capturing forehead sweat and transferring its directional flow via barriers and canals to a far less bothersome location. This is achieved by simple gravitational forces acting upon perspired bodily fluids that direct perspiration flow within the barriers of the devices confined canal routes.

OPERATION OF THE INVENTION

This invention is essentially an eye wear lens frame that has the capability to capture forehead perspiration and transfer said fluids through itself so disposal of fluids is deposited in a less annoying place. The lens support body being the bulk of the frame is preferably but not limited to a formed piece of impermeable elastic material having a elliptically shaped external seal running along the length of the inside facing surface. Essentially we have a transverse length wise seal having a deep center and shallow edges enabling the lower and upper lips to be thrust out under compression. On the opposite side of the upper most lip or edge lies a shallow sloping shelf which terminates within a flow trough that is contiguous to a row of cut out voids that run the length of the lens housing section. The cut out voids are the fluid receptors to the central cavity or canal area. Once these fluids reach this area they may become gravitationally expelled out through the canals of the joined frame arms or temple bars tip ends that rest over the ears. The frame arms and the lens support body each have two internal bores in there connective ends and are joined to each other by the insertion of a flow connector and a tensional member having a connective means.

The invention functions when the wearer slightly pulls back on the temple bars or arms while placing the central surface seal upon a comfortable lower fore head location. The curvature of the arms resting behind the ears under light tensional force will hold the device securely in place. The nose cutout in the lens member has an inward projecting foam rest for comfort and to help keep the lens and forehead seal parallel to the face. When conditions that cause forehead perspiration occur flowing perspiration will run over the lip seal and flow into the trough area. Gravity will feed said fluids along the entrapment trough through the cut out collection voids until enough fluid mass collects within the central canal to allow such fluids to flow. Captured fluids will run along the canal of the lens support body out through the canal of the dog bone connector and out through the ends of the frame arms.

OBJECTS AND ADVANTAGES

The object of this invention is to incorporate a useful and needed function as an additional feature in an already desired and established product such as sporty sun glass frames.

Another object of this invention is to introduce another choice or option for those who find relief in wearing some form of forehead sweat absorption device.

Another object of my invention is to create a product that utilizes a new process for confronting annoying forehead perspiration.

DESCRIPTION OF DRAWING FIGURES

DRAWING REFERENCE NUMERALS

Figure 1:
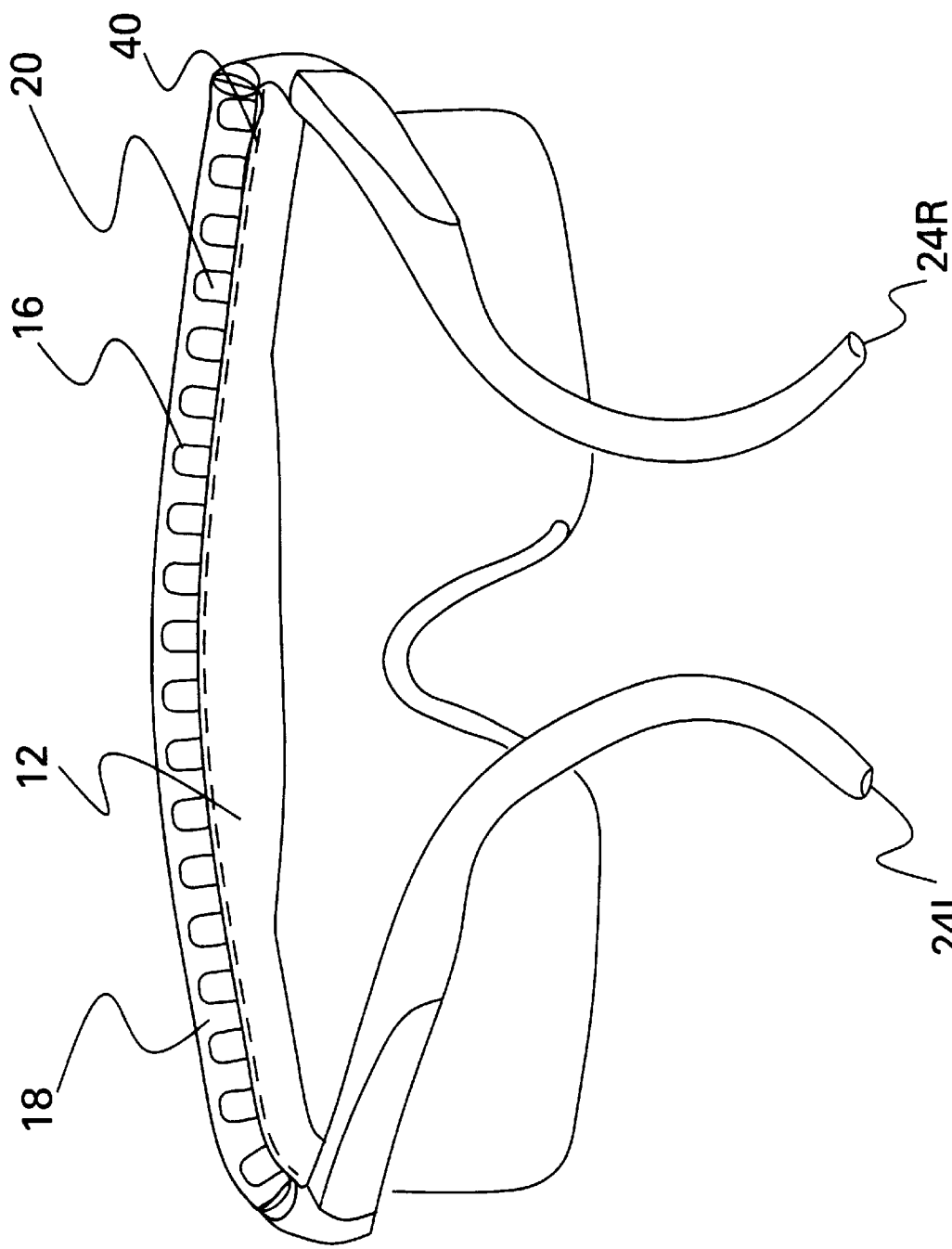
FIG.1 shows the complete assembled product with some defined features.

12: forehead seal
14: seal lip
16: absorption cutout
18: lens support element
20: internal canal
22R: right side temple bar
22L: left side temple bar
24R: right side discharge opening
24L: left side discharge opening
26R: right side dog bone connector
26L: left side dog bone connector
28R: right side tensional member housing
28L: left side tensional member housing
30: lens
32: nose bridge support
34A: temple bar connective orifice
34B: support body connective orifice
36: dog bone connector canal
38: tension member
40: fluid collection trough
42: lens support groove
44A: right side temple bar ducts
44B: left side temple bar ducts
46A: temple bar connective bore
46B: support body connective bore

DESCRIPTION OF THE INVENTION

Figure 2:
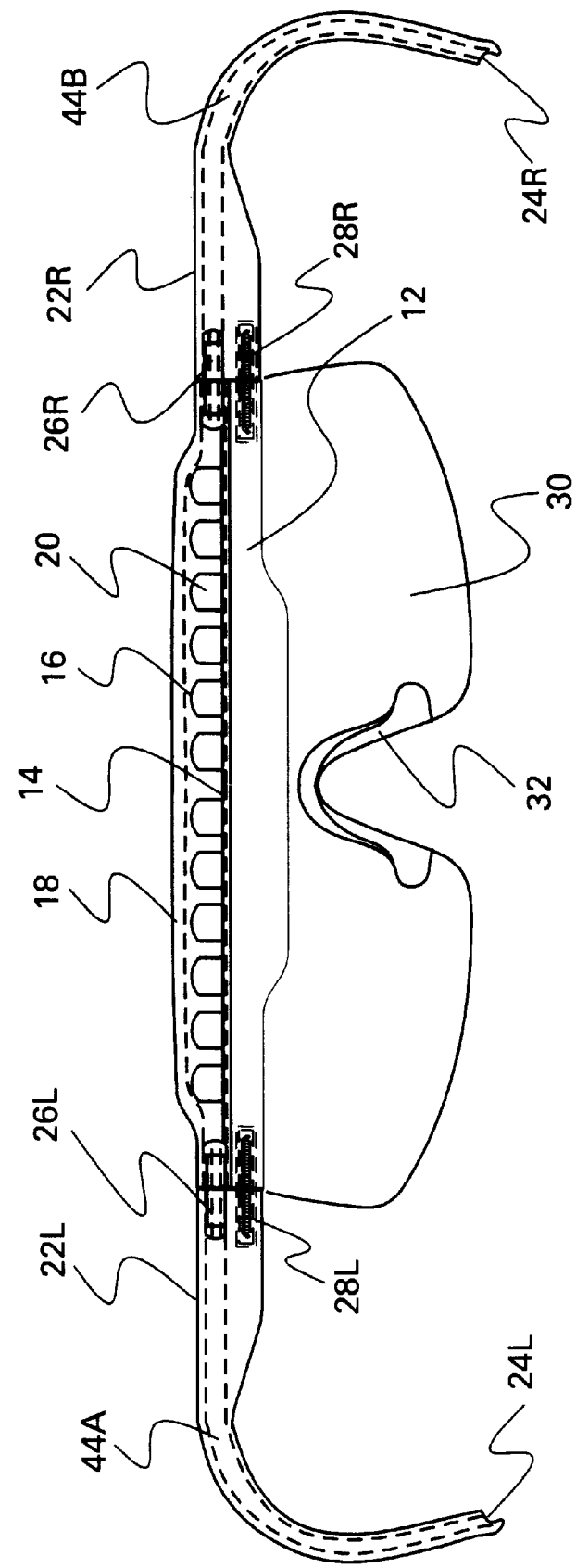
FIG.2 shows the complete assembly with internal views.
Figure 3:
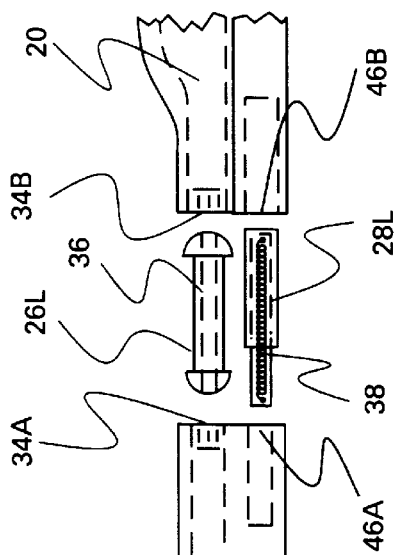
FIG.3 shows a breakdown of the arm attachment.
Figure 4:
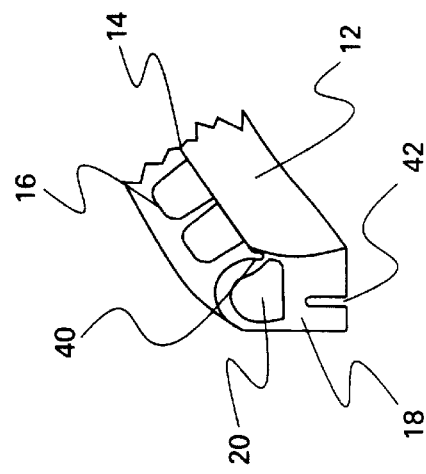
FIG.4 shows a cross sectional view of the body.

Referring now to the drawings, FIGS. 1 thru 4 will best illustrate the makeup and process by which this device functions. FIG. 1 offers the viewer a look at the complete article depicting some of its essential features. The long centrally located lens support body is the primary body section that gives reference to features 12, 16, 18, 20 and 40. These features are the principle means for an effective forehead sweat absorption process contained in an eye wear lens frame. When the complete article like in FIG. 1 is attached to the wearer's head, flowing fore head perspiration will collect in trough 40 and become accumulated through absorption cutouts 16 of lens support element 18. These body fluids will run along canal 20 and out the ends of the temple bars at 24L and 24R. Referring now to FIG. 2, the viewer is provided a complete assembly configuration with internal components and canals exposed. The lens support element 18 having a specifically configured elliptically shaped profile is host to a number of essential features which in conjunction to mated components allows the device to collect and transfer fore head sweat through out the length of itself. Lens support element 18, could be composed of a number of different materials that have the ability to adapt its shape to the curvature of the human forehead comfortably. As seen in FIG. 4, the seal 12 has an upper and lower terminus with a projecting tapered edge forming seal lip 14 while in a compressive state. The backside of the upper seal lip has a sloping shelf which terminates in a lengthwise groove which forms the fluid trough 40. Some of the essential features the lens support element would have would be the seal lip 14, FIGS. 2, and 4 absorption cutouts 16, an arched incurvate forehead seal 12 and internal canal 20. Lens support element 18 FIGS. 2 and 3 would have a connective means to frame arms 22R and 22L via dog bone connectors 26L and 26R and tensional member housing 28L and 28R of which both are designed to be pressed in. Thus completed and properly joined a continuous canal would extend from the left end opening 24L through canal 44A, through canal 36. FIG. 3 of connector 26 and into canal 20 of the lens support element. The right side device would be assembled in duplicate order using right side member parts. Lens 30 would be held in position within lens support groove 42. Nose bridge support 32 would serve to offer support and proper alignment for an effective lip seal 14, FIG. 4. FIG. 3 shows a complete detailed assemblage of exterior and interior views. FIG. 4 offers a greater description of detail through a cut away profile view of body part 18.

SCOPE OF THE INVENTION

While the above described invention may seem limited in scope those skilled in the art can imagine and create other variations of its use in principle. They can experiment with alternate forms, shapes, and colors. They can change the size and locations of essential features. They can experiment with a number of different materials having either rigid or elastic properties. They could attempt to impress they have a different invention through a disguise of accessories. The reader is requested to determine the scope of the invention by the appended claims and their legal equivalents, and not by the examples which have been given.

What is claimed is:

1. An eye wear lens frame having a means to collect, transfer and dispose of perspired human forehead fluids, said frame including a means for proper fit to a wearer's head, said frame comprising:

a) a plurality of members that when joined form a fluid transfer device, said device having a means to capture, transfer and dispose of said fluids via exerted gravitational forces acting upon a random amount of captured fluid mass having contact with said device, said fluids being disposed therein thus urging a downward flow, said plurality of members including a forehead fluid seal for collection of said fluids, said forehead fluid seal having a means for fluid collection and a network of canals which form said means for fluid transfer and disposal, said canals providing a path for disposal of said fluids and wherein said forehead fluid seal shall comfortably adapt and form itself to a wearer's forehead;

b) said forehead fluid seal adapting in shape to a transverse contour of a wearer's forehead, said seal being primarily elliptically shaped in profile, having an incurvate arch along an exterior face of said seal so that an upper and lower terminus each have a projecting tapered edge, said edge forming a seal lip while in a compressive state when properly fitted to a wearer's head and said collection means includes a sloping shelf upon a backside of said upper seal lip, said shelf terminating in a lengthwise groove, said groove being a fluid trough;

c) wherein said collection means includes a lens support element having a number of cutouts, said cutouts being absorption openings that are proximal to said fluid trough, said openings serving to draw in collected forehead fluids and deposit said fluids within the canal of said forehead fluid seal;

d) wherein said means of fluid transfer functions effectually by said exerted gravitational forces acting upon captured fluids within said network of canals, which form controlled flow barriers extending throughout the device having a means to capture and directionally expel said fluids;

e) said means for said fluid disposal comprising a number of terminal openings through which the fluid is discharged; and f) wherein said lens support element has a means for rapid interchange of various lens configurations.

\* \* \* \* \*